United States Patent
Blanch et al.

(10) Patent No.: US 7,562,657 B2
(45) Date of Patent: Jul. 21, 2009

(54) METHOD AND APPARATUS FOR NON-INVASIVE PREDICTION OF INTRINSIC POSITIVE END-EXPIRATORY PRESSURE ($PEEP_i$) IN PATIENTS RECEIVING VENTILATOR SUPPORT

(75) Inventors: Paul B. Blanch, Alachua, FL (US); Vikas Meka, Gainesville, FL (US); Neil R. Euliano, Gainesville, FL (US)

(73) Assignee: Convergent Engineering, Inc., Gainesville, FL (US)

( * ) Notice: Subject to any disclaimer, the term of this patent is extended or adjusted under 35 U.S.C. 154(b) by 279 days.

(21) Appl. No.: 11/165,617

(22) Filed: Jun. 23, 2005

(65) Prior Publication Data

US 2005/0284476 A1   Dec. 29, 2005

Related U.S. Application Data

(60) Provisional application No. 60/582,409, filed on Jun. 24, 2004.

(51) Int. Cl.
*A61M 16/00* (2006.01)
*A61M 5/08* (2006.01)

(52) U.S. Cl. .......................... 128/204.23; 128/204.26; 600/538

(58) Field of Classification Search .............. 600/529, 600/532, 533, 538; 128/200.24, 204.18, 128/204.21, 204.23, 204.26; 700/50
See application file for complete search history.

(56) References Cited

U.S. PATENT DOCUMENTS

| | | | | |
|---|---|---|---|---|
| 3,889,670 A | * | 6/1975 | Loveland et al. | 128/203.12 |
| 5,159,935 A | * | 11/1992 | Sackner et al. | 600/534 |
| 6,015,388 A | * | 1/2000 | Sackner et al. | 600/529 |
| 6,240,920 B1 | * | 6/2001 | Strom | 128/204.23 |
| 6,443,904 B2 | * | 9/2002 | Nissila | 600/483 |
| 6,484,719 B1 | * | 11/2002 | Berthon-Jones | 128/204.23 |
| 6,588,422 B1 | * | 7/2003 | Berthon-Jones et al. | 128/204.23 |
| 6,612,995 B2 | * | 9/2003 | Leonhardt et al. | 600/532 |
| 6,705,314 B1 | * | 3/2004 | O'Dea | 128/204.18 |
| 6,723,055 B2 | * | 4/2004 | Hoffman | 600/538 |
| 6,820,618 B2 | * | 11/2004 | Banner et al. | 128/204.23 |

\* cited by examiner

*Primary Examiner*—Justine R Yu
*Assistant Examiner*—Annette F Dixon
(74) *Attorney, Agent, or Firm*—Christine Q. McLeod; Beusse Wolter Sanks Mora & Maire, P.A.

(57) ABSTRACT

The present invention describes a method and apparatus for non-invasive prediction of the "intrinsic positive end-expiratory pressure" (PEEPi) which is secondary to a trapping of gas, over and above that which is normal in the lungs; the presence of PEEPi imposes an additional workload upon the spontaneously breathing patient. Several indicators or markers are presented to detect and quantify $PEEP_i$ non-invasively The markers may include an expiratory air flow versus expiratory air volume trajectory, an expiratory carbon dioxide flow versus expiratory air volume trajectory, an expiratory carbon dioxide volume to expiratory air volume ratio, an expiratory air flow at onset of inhalation, a model of an expiratory waveform, a peak to mid-exhalation airflow ratio, duration of reduced exhaled airflow, and a Capnograph waveform shape.

37 Claims, 7 Drawing Sheets

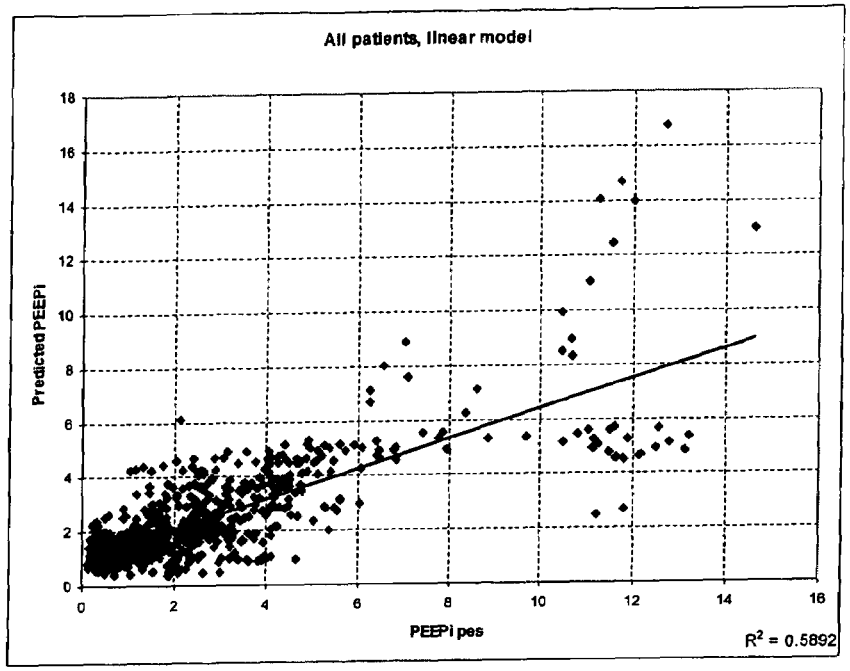
FIG. 9 - Prediction of PEEPi on all patients using a linear model. ($r^2$=0.589)
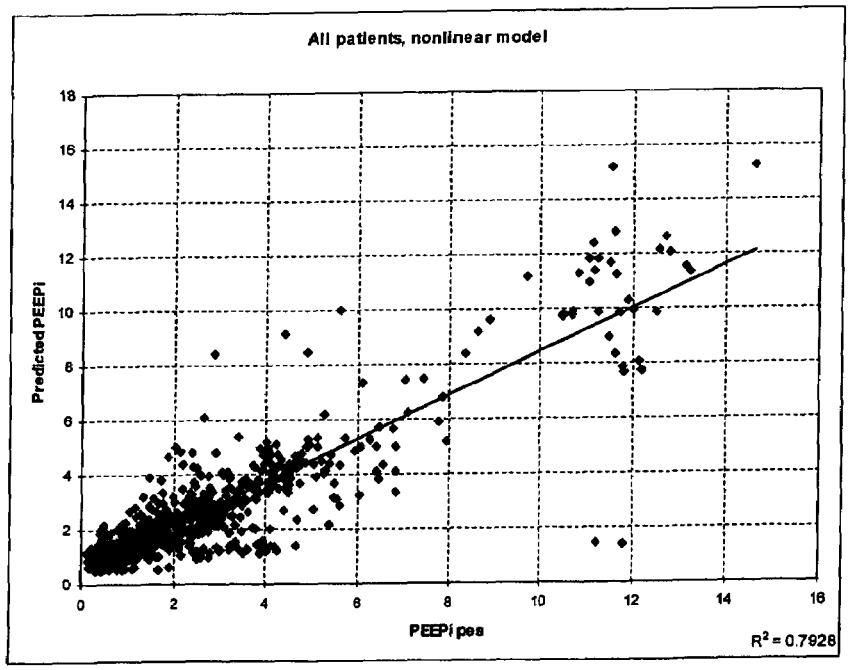
FIG. 10 - Prediction of PEEPi on ALL patients using a nonlinear model. ($r^2$=0.793)

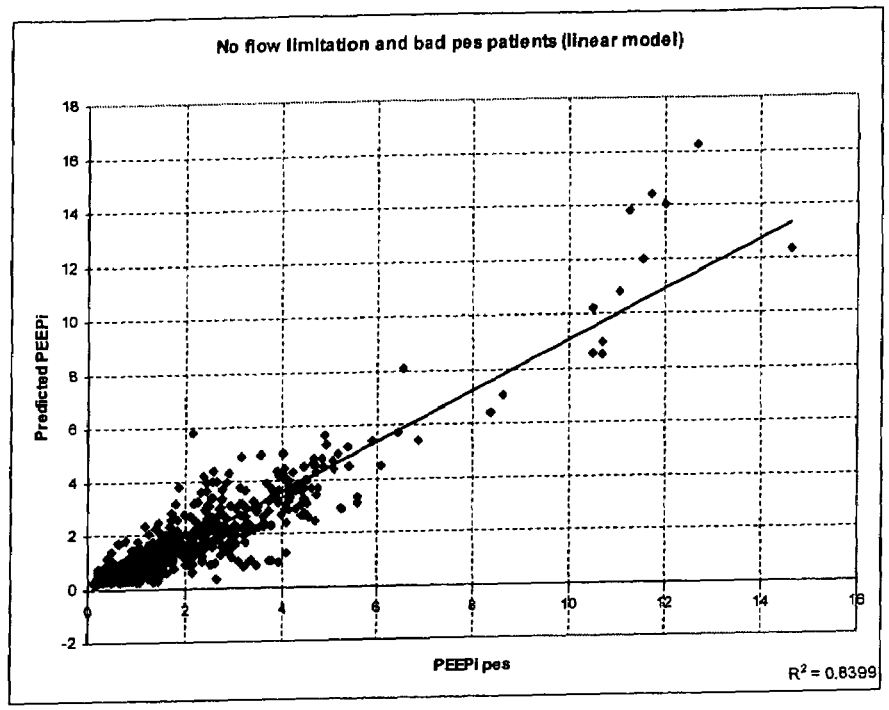
FIG. 11 - Prediction of PEEPi on all patients that do not have flow limitation using a linear model. ($r^2=0.84$)
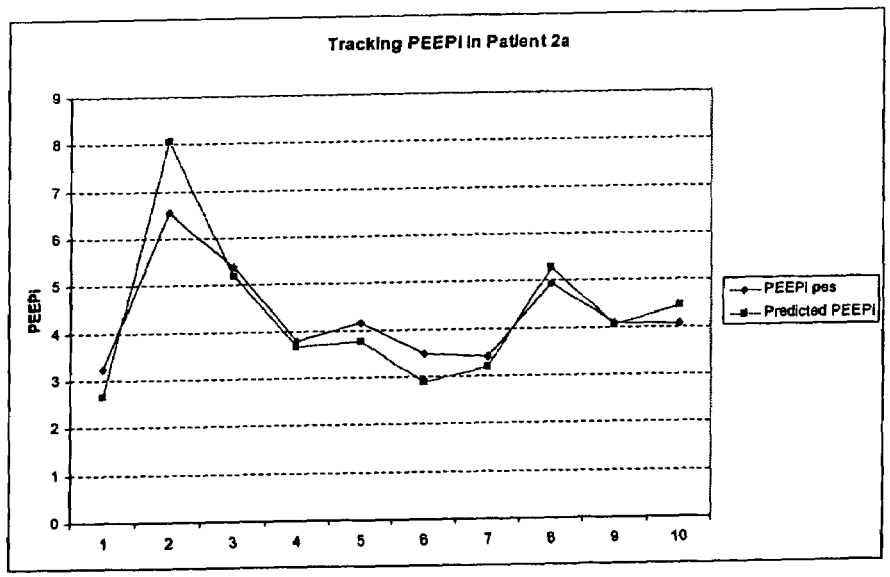
FIG. 12 - PEEPi prediction in patient 2a

METHOD AND APPARATUS FOR NON-INVASIVE PREDICTION OF INTRINSIC POSITIVE END-EXPIRATORY PRESSURE (PEEP$_i$) IN PATIENTS RECEIVING VENTILATOR SUPPORT

CROSS-REFERENCE TO RELATED APPLICATIONS

This application claims benefit of the Jun. 24, 2004 filing date of U.S. provisional patent application No. 60/582,409.

FIELD OF INVENTION

The present invention relates generally to the field of respiratory therapy, physiology, and critical care medicine including ventilator management and respiratory monitor technology, and, more particularly, to a method and apparatus for non-invasive prediction of intrinsic positive end-expiratory pressure (PEEP$_i$) using certain markers.

BACKGROUND OF INVENTION

Mechanical ventilatory support is widely accepted as an effective means for supporting and treating patients with respiratory failure. Mechanical ventilators are simply machines designed to assist with inspiration and expiration. Often, a primary objective of ventilatory support is for the ventilator to provide some or all of a patient's work of breathing (WOB). This goal is often not achieved due in part to an inability to accurately measure and titrate a patient's WOB. Ventilators must be highly reliable, durable and precise. Most modern ventilators are electronically controlled and most are designed to allow many small, but different, fine-tuning manipulations by the operator. Ideally, the operator uses these controls to match the pressure and flow output characteristics of the ventilator to meet each individual patient's needs. Optimized ventilator settings also serve to make ventilatory support more tolerable for the patient.

The first generation of mechanical ventilators (prior to the mid-1960s), were designed only to support alveolar ventilation and to provide supplemental oxygen for those patients unable to breathe themselves (generally for reasons such as neuromuscular disease or paralysis). These early ventilators provided 100% of the work required to breathe if the supported patient did not breathe on his or her own. If the patient attempted to breathe spontaneously, a complete lack of a response from the ventilator created agitation—also termed "fighting the ventilator". Those patients that tried to breathe spontaneously became so agitated, it was (and remains in some institutions) common practice to heavily sedate or paralyze the patient to ensure proper synchrony with the ventilator. Sedation or drug-induced muscle paralysis, may create more problems than they solve. For instance, heavily sedated or paralyzed patients simply can not breathe spontaneously; as a result, if they become accidentally disconnected from the ventilator they will quickly die of asphyxia. This required an increased vigilance and a very elevated level of monitoring. More importantly, paralysis and sedation also lead to a rapid deterioration of the patient's respiratory muscles, or what has become known as: "disuse atrophy". Without strong, conditioned respiratory muscles, clinicians find it difficult or, on occasion, nearly impossible to liberate their patients from the ventilator, even when their original pulmonary problems have resolved. To overcome these potential problems, modern mechanical ventilators have become far more sophisticated in response to our increasing understanding of lung physiology. In an effort to improve patient tolerance of mechanical ventilation, while simultaneously maintaining adequate respiratory muscle function, many new modes have been developed. Many of these new modes allowed spontaneous breathing, patient-triggered and pressure-assisted breaths, or even patient-triggered mandated breaths. These pressure assisted breaths, when properly adjusted by the clinician, allow the ventilator to share the WOB with the patient. By the early 1970s, a new mode of ventilation allowed patients to breathe at their own pace and magnitude, in the time period between mandated (machine delivered and controlled) breaths that were programmed for delivery at precise intervals each minute; this mode was known as Intermittent Mandatory Ventilation (IMV). Pressure Support Ventilation (PSV), came along a few years later and could be used alone or in combination with IMV; this mode provided a variable pressure-assist (at an operator chosen level of pressure) for each patient-initiated spontaneous inhalation effort. Varieties of "alternative" ventilation modes, addressing the needs of severely impaired patients, continue to be developed.

Patients receiving ventilator support need different levels of assistance; some require complete control of their ventilation, while others require varying levels of support depending upon their ability to sustain breathing on their own. Matching the ventilator support provided, to that required by the patient, remains to this day, an imposing challenge; too much support predisposes to disuse atrophy, while too little support often leads to a cycle of fatigue, followed by respiratory failure. At the present time, there is no readily available, easy to use, or reliable method or apparatus for estimating an appropriate support level. Confounding the matter further, a patient's requisite level of support may vary widely throughout the day, for a variety of reasons.

Gas inadvertently trapped in a patient's lungs, or PEEP$_i$, interferes with the clinicians best attempts to estimate an appropriate support level for patients. For years, many clinicians were completely unaware of its existence. Hence when it was first reported, it was termed "intrinsic" or even "occult" because it is hidden from view (using conventional monitoring techniques). The extra (un-exhaled or trapped) gas, remaining in a patient's lungs at the onset of the next inhalation, creates an inspiratory threshold load (a positive pressure level above ambient) that the patient's inspiratory muscles must overcome before fresh gas can enter the lungs. Furthermore, since the inspiratory muscles are displaced from their normal resting position (by the hyperinflation) they are mechanically disadvantaged; that is, the direction of the respiratory muscles are pulling, no longer generates the largest possible change in volume/unit of force. All of this simply means that patients with dynamic pulmonary hyperinflation (DPH) or PEEP$_i$, must work significantly harder to breathe. In addition, patients receiving ventilator assistance or, those patients that are generating, at least, a portion of the work of breathing, must generate another additional effort to breathe; that is, they must overcome the trigger pressure set on the ventilator before they receive any assistance from the ventilator. A trigger pressure must be used to synchronize the patient's efforts to the ventilator's response (otherwise, the ventilator would randomly initiate breaths, some of which might conflict with, or even negate, the patient's own efforts). The combination of an undetectable and difficult to quantify PEEP$_i$ level and the ventilator's trigger setting, frequently produce an intolerable additional workload; the additional work is often high enough to produce inspiratory muscle fatigue, particularly in patients with poor respiratory muscle function. For those patients not trying to breathe on their own, undetected PEEP$_i$ is just as problematic. The additional pressure it produces in the patient's chest can reduce venous blood return into the chest, which in turn reduces cardiac output and, ultimately, can dramatically reduce a patient's blood pressure. Too much trapped gas in the lungs also predisposes to over-inflation and structural damage, even rupture of the lungs. Research has shown that $PEEP_i$ occurs far more frequently than is commonly believed. It has also been shown that in ventilator-dependent COPD patients, $PEEP_i$ accounts for a large percentage of the patient's total ventilatory workload. Reducing or eliminating $PEEP_i$ could then, have a major clinical impact for patients with an acute exacerbation of COPD. Clearly, detecting and accurately measuring $PEEP_i$ represents an extremely important tool in managing affected patients.

In today's intensive care unit (ICU), most modern ventilators can measure a patient's $PEEP_i$, but only when they do not breathe on their own—any movement or spontaneous efforts during measurement will invalidate that measurement. Ventilator-supported patients that breathe spontaneously virtually never have their $PEEP_i$ accurately measured; to do so, requires the placement of an esophageal balloon or use of thoracic impedance measuring equipment. Both approaches are expensive, very technique oriented and extremely time-consuming. As a rule, these approaches are only used by researchers. The esophageal balloon is the most commonly employed approach because it is the least expensive and balloons tend to interfere with fewer other ongoing and required monitors or therapies. The concept involves using a properly inflated and positioned, balloon tipped catheter that is inserted into the patient's esophagus. When positioned properly, it is used to measure esophageal pressure ($P_{es}$). It has been shown that in certain esophageal locations (but not all locations), pressure changes within the esophagus are of the same magnitude as those occurring in the pleural space (although the absolute pressure values will likely NOT be the same). The change in esophageal pressure (from resting, or baseline) needed to abruptly bring expiratory flow to the point where it just crosses the zero flow axis (the instant just prior to the onset of flow into the lungs) represents $PEEP_i$, also called *dynamic* $PEEP_i$ ($PEEP_{i,dyn}$).

The esophageal balloon technique has never been popular with clinicians. The balloons are difficult to place, can interfere with important equipment like feeding tubes, and must be positioned and inflated properly to prevent inaccurate and misleading measurements. Further complicating the esophageal balloon procedure is signal quality. Frequent swallowing or inadvertent esophageal spasms can be difficult to discern and yet render the signal temporarily useless. Additionally, the esophagus is located just anterior of the heart and the signal, as a result, is often difficult to interpret without using a "heavy filter" to remove the unwanted pressure fluctuations secondary to the beating heart. Thoracic impedance equipment is not only expensive, difficult to use, and may not be consistently repeatable (according to researchers), it often interferes with absolutely indispensable electrocardiography monitoring leads, crucial intravenous catheters, and other important equipment. For these reasons, it seems likely that the esophageal balloon and thoracic impedance devices will remain investigative tools.

For those patients not breathing spontaneously, $PEEP_i$ is measured using an appropriately timed, end-expiratory, airway occlusion maneuver. This involves a sudden occlusion of the expiratory valve (a blocking of the path normally taken by the patient's exhaled gases). Occlusion of the expiratory valve traps any additional gas that might be still leaving the patient's lungs, in the breathing circuit (which is attached to the patient's ventilator) and the patient's lungs. When the pressure (measured in the breathing circuit) stabilizes, if it is above the normal baseline pressure (the pressure at end-exhalation), the patient is said to have $PEEP_i$. The occlusion technique could, potentially, be used for spontaneously breathing patients; but, to do so would require the patient to hold their breath, making absolutely no attempt to breathe, or even move, until the pressure in the breathing circuit reaches equilibrium. Unfortunately, this level of cooperation is almost nonexistent when patients are extremely sick, comatose, heavily sedated or, struggling to breathe against the additional workload imposed by $PEEP_i$.

U.S. Pat. No. 6,588,422 pertains to the field of ventilatory support for respiratory failure, particularly due to lung disease, and in particular to automatically providing sufficient end expiratory pressure to unload $PEEP_i$. The '422 patent seeks to provide continuous and automatic adjustment of the expiratory pressure during ventilatory support, so as to substantially prevent dynamic airway compression and unload $PEEP_i$ with the smallest amount of external expiratory pressure. The object of this invention involves varying the external pressure exerted by the ventilator during the exhalation phase and does not measure or quantify $PEEP_i$ in any manner. Nor is it obvious how one could measure PEEPi using this patent.

Additionally, U.S. Pat. No. 6,240,920 discloses a method for determining at least one parameter related to a patient's spontaneous attempts at inspiration and/or the patient's respiratory effort in spontaneous attempts at inspiration. What is disclosed in the '920 patent is again a potential method to counteract and manage $PEEP_i$; it provides no methodology for measuring or quantifying the patients actual $PEEP_i$ level.

Developing a non-invasive measure of $PEEP_i$ (that works in spontaneously breathing patients receiving ventilatory support) is complicated by a number of factors. First, the gas trapped at the alveolar level is almost always non-homogeneously distributed across both lungs thereby, making it difficult to measure the true $PEEP_i$. This means that any measurement of $PEEP_i$, is, at best, an average of the two lungs, considered as though they were identical. Alternatively, the excess pressure (trapped air) may be hidden behind prematurely collapsed airways—making it virtually undetectable. And lastly, patient efforts to breathe create artifacts that vary on a breath-to-breath basis. Such artifacts may be difficult to separate from the ideal passive pressure waveforms.

SUMMARY OF THE INVENTION

There is a need in the art for accurately detecting and quantifying $PEEP_i$ non-invasively, especially in spontaneously breathing patients. Non-invasive determination of a patient's intrinsic PEEP will 1) enable clinicians to be better informed of patient status, enabling better management of patient respiratory therapy, 2) improve patient analysis and physiologic monitoring/modeling, and 3) minimize patient discomfort (non-invasive) and clinician intervention (no need for occlusion) from invasive $PEEP_i$ measurement. The measure will provide clinicians with accurate, continuous information that will enable them to make better decisions on patient's respiratory therapy. The present invention is designed to address this need.

Broadly speaking, the present invention provides a method and apparatus for non-invasively predicting (estimating) $PEEP_i$. The presence of $PEEP_i$, which often remains undetected, creates an inspiratory threshold load (a positive pressure level above ambient) that the patient's inspiratory muscles must overcome before fresh gas can enter the lungs. In addition, excessive levels of $PEEP_i$ can lead to impaired cardiac function, an increased risk of barotrauma (structural lung damage secondary to excessive lung volumes), reduced inspiratory muscle pressure-generating capacity, and abnormally increased work of breathing.

The inventors have innovatively developed multiple indicators to detect and quantify $PEEP_i$ non-invasively. Although some of these markers can be used alone to predict $PEEP_i$, it is observed that some markers are good primarily for detection, while others are optimal for quantification. Furthermore, it is also noticed that certain markers work best on a specific group of subjects. Therefore, in an aspect of the invention, using several of these markers simultaneously has been demonstrated to improve the prediction of $PEEP_i$ and broadens its operability to a wider range of patients.

The primary advantage is that the method is non-invasive, breath-to-breath, and in real-time. Therefore, there is no need to insert a catheter into the patient. The method requires only that measurements be made at the subject's airway, including one or more of the following: pressure at the airway, end tidal $CO_2$, and airflow, measured at the mouth. These airway measurements are routinely monitored in most ICUs—by using any of the common respiratory equipment currently used to monitor and maintain patients while they receive ventilatory support.

Although the occlusion method is essentially non-invasive, it nevertheless requires a potentially irritating "intervention" and does not work for spontaneously breathing patients. This method does not suffer from either of these difficulties. There is no need to occlude the patient's airway and, it can be determined continuously without intervention.

The approach includes the measurement of several different $PEEP_i$ markers which in turn are fed into a specialized mathematical model (for example, a neural network) that then predicts a $PEEP_i$ value, based on these values. The model can be a linear model (e.g., multiple regression) or a nonlinear model (e.g., a neural network, fuzzy logic, etc.).

The $PEEP_i$ markers or indicators may include:

Flow/volume trajectory—the concept of plotting a flow/volume waveform has been experimentally proven to be a useful quantification maker that works in the many patients.

$CO_2$ flow/volume trajectory—this marker has been experimentally proven to be an indicator of PEEPi. It is particularly useful for identifying patients with elevated levels of PEEP, and for those suffering from premature airway collapse or expiratory flow limitation.

$CO_2$/volume ratio—this marker has been experimentally proven to be an indicator for detecting $PEEP_i$ in patients exhibiting severe expiratory flow limitation patients.

Flow at the onset of inspiratory effort—this marker has been experimentally proven to useful for quantifying PEEPi.

Modeling the patient's expiratory waveform—this can be accomplished using two different methods: 1) least squares analysis and, 2) exponential modeling. Both methods have been experimentally proven to be useful in quantifying $PEEP_i$.

Peak to Mid-Exhalation Flow Ratio: flow limitation patients may have high peak flows that decay extremely rapidly. When the mid-exhalation flow is low, this parameter is high, indicating likely flow limitation and a resultant $PEEP_i$.

Duration of low exhaled flow: flow limitation patients may have an abnormally high percentage of their exhalation occur at low flows. This parameter determines the percentage of the exhalation (by volume or time) that occurs at low flows.

Capnograph waveform shape: flow limitation patients may have a identifiably unique $CO_2$ waveform versus normal patients. In particular, a Phase III slope (the slope after the rapid rise time in $CO_2$) is not horizontal and rises throughout exhalation, indicating a continuing low-flow exhalation.

Negative expiratory pressure or an increased expiratory gradient: a patient's expiratory flow rate should be directly proportional to pressure gradient (difference in pressure between the lungs and the pressure in the breathing circuit) during exhalation. If there is no pressure (in the breathing circuit) during exhalation, the gradient can best be increased by briefly applying a negative pressure, during the exhalation phase, in the breathing circuit. For patients receiving additional pressure during exhalation, the gradient can be increased by briefly removing the added pressure. If the expired gas flow does not increase in response to the increased gradient, the patient suffers from expiratory flow limitation and is exceptionally prone to developing $PEEP_i$.

In addition to the above mentioned markers, the concept of using two or more of these and/or potentially other markers for $PEEP_i$ as inputs to a mathematical model (linear or nonlinear, such as a neural network) for predicting $PEEP_i$ is new and unique. The combined information provided by using two or more markers (those mentioned above and others) may result in a more accurate estimate of $PEEP_i$.

In one aspect of the invention, the method comprises creating a mathematical model of the patient's $PEEP_i$ using predetermined parameters that are collected non-invasively, such as those collected with standard respiratory monitors. The respiratory monitors typically contain airway pressure and airway flow sensors that measure the flow and pressure of gases going into and out of the patient as a function of time. From these time versus flow or pressure waveforms, a variety of parameters are selectively derived that are used in characterizing different aspects of the patient's breathing and/or the patient's interaction with the ventilator. These parameters contain information that is extracted to accurately estimate the intrinsic PEEP.

More specifically, the method of the invention comprises a method of estimating the actual $PEEP_i$ using a combination of multiple parameters derived from the aforementioned sensors, as well as others attached to the patient and/or ventilator. The $PEEP_i$ parameter can be any parameter that represents the amount of excess pressure in the lungs, including but not limited to flow/volume trajectory, $CO_2$ flow/volume trajectory, $CO_2$/volume ratio, flow onset, modeling on expiratory waveform, and peak to mid-exhalation flow ratio.

This method includes using a linear combination of parameters or a nonlinear combination of parameters, including but not limited to a neural network, fuzzy logic, mixture of experts, or polynomial model. Moreover, multiple different models can be used to estimate the $PEEP_i$ of different subsets of patients. These subsets can be determined by various means, including but not limited to patient condition (pathophysiology), patient physiologic parameters (lung resistance and compliance), or other parameters.

In an aspect of the invention, the method for estimating $PEEP_i$ in a patient comprises use of a neural network, wherein the neural network provides $PEEP_i$ information for the patient based upon input data, wherein the input data includes at least one of the following parameters: flow/volume trajectory, $CO_2$ flow/volume trajectory, $CO_2$/volume ratio, flow onset, modeling on expiratory waveform, peak to mid-exhalation flow ratio, duration of low flow exhalation, and capnograph waveform shape, wherein the intrinsic PEEP information is provided as an output variable.

In the above-noted method, the neural network is trained by collecting clinical data from a test population of patients used to obtain teaching data, the teaching data comprising the above-noted input information, inputting the teaching data into the neural network, whereby the neural network is trained to provide an output variable corresponding to the intrinsic PEEP.

As a system for estimating intrinsic PEEP in a patient, the system comprises a neural network which first receives as input primary teaching data obtained from clinical testing of a test population of patients, whereby the neural network learns the teaching data and is trained to provide an output variable for intrinsic PEEP, such that when said neural network receives patient input data in the form of the above-noted parameters obtained from a patient, the neural network provides the output variable for estimating intrinsic PEEP for that patient.

The invention can be implemented in numerous ways, including: as a system (including a computer processing or database system), as a method (including a computerized method of collecting and processing input data) and, as a method for evaluating such data to provide an output(s), an apparatus, a computer readable medium, a computer program product, or a data structure tangibly fixed in a computer readable memory. Several embodiments of the invention are discussed below.

As a system, an embodiment of the invention includes a processor unit having input and output devices. The processor unit operates to receive input parameters, process the input and provide an output corresponding to PEEPi. This output can be then used to control external devices, such as a ventilator. The processing of the data can be accomplished by various means such as neural networks, parallel distributed processing systems, neuromorphic systems, or the like.

As a method of predicting $PEEP_i$, the method includes processing predetermined input variables (parameters), preferably through the use of a neural network.

As a computer readable media containing program instructions, an embodiment of the invention includes: computer readable code devices for receiving input variables, processing the input, and providing an output indicative of $PEEP_i$. In a preferred embodiment, processing comprises utilizing a neural network. The method may further include controlling a ventilator in response to the output obtained.

The methods of the present invention may be implemented as a computer program product with a computer-readable medium having code thereon. The program product includes a program and a signal bearing media bearing the program.

As an apparatus, the present invention may include at least one processor, a memory coupled to the processor, and a program residing in the memory which implements the methods of the present invention.

Other aspects and advantages of the invention will become apparent from the following detailed description taken in conjunction with the accompanying drawings, illustrating, by way of example, the principles of the invention.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 9-12 show graphs of experimental data derived for multiple patients showing the results of exemplary systems using both linear and nonlinear models (neural network), and using multiple patients, some experiencing flow limitations and some experiencing no flow limitations, and a subset of patients experiencing no flow limitations.

DETAILED DESCRIPTION OF THE INVENTION

Figure 1:
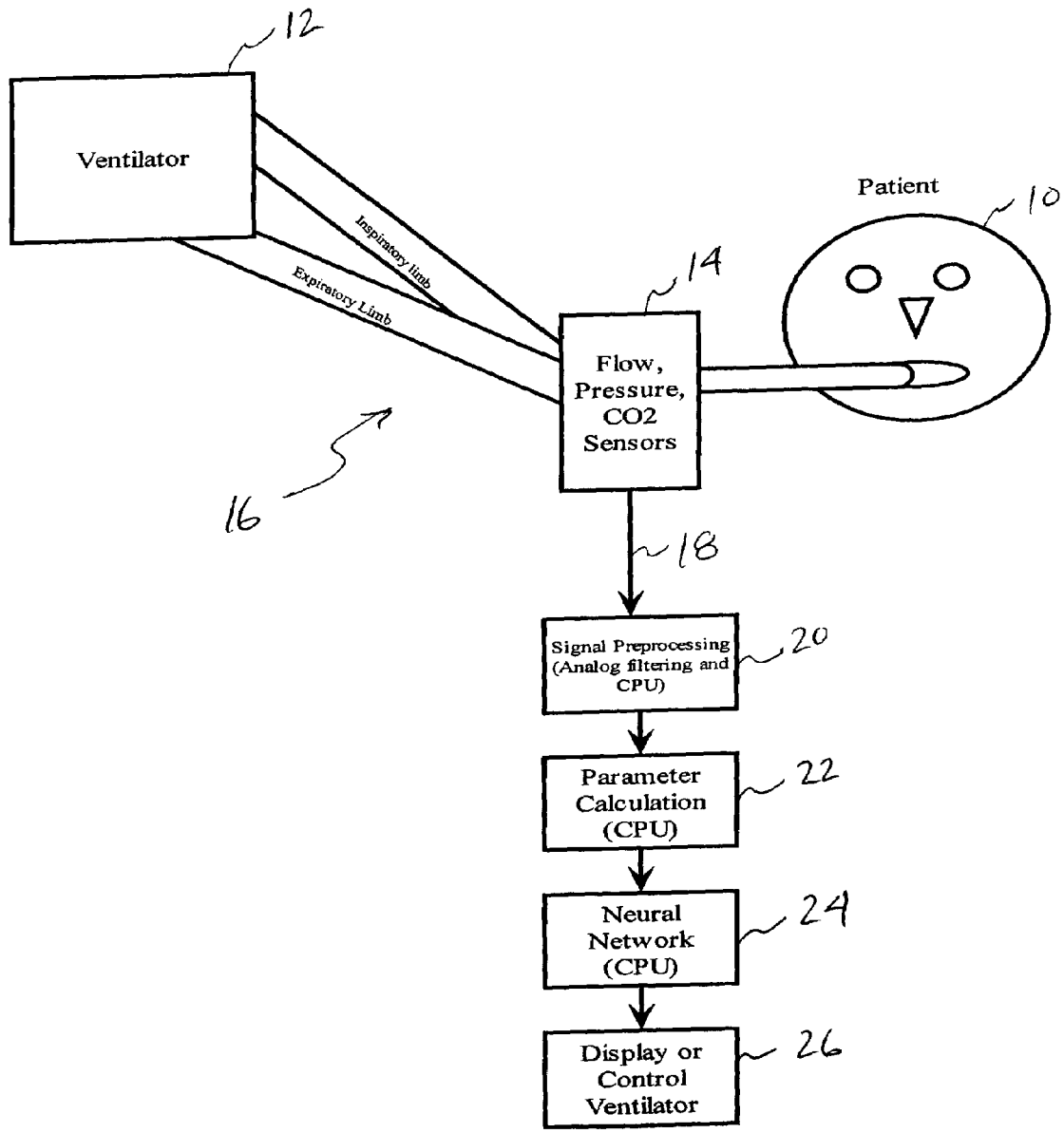
FIG. 1 depicts a method of one aspect of the invention for a patient on a ventilator.

Referring now to the drawings, the preferred embodiment of the present invention will be described.

In the embodiment depicted in FIG. 1, a patient 10 requiring respiratory support and connected to a ventilator 12 will have an airway flow and pressure sensor 14, along with possibly a carbon dioxide detector attached at the y-piece of the standard ventilator circuit 16. These sensors measure the flow, pressure, and partial pressure of carbon dioxide in the gases that pass to and from the patient. These raw signals 18 may be preprocessed in a signal processor 20 using analog and digital signal processing to clean the signal, remove sensor biases and offsets, etc. These signals are then be processed in a parameter extraction module 22 to calculate a variety of other parameters from the flow, pressure, and $CO_2$ data and identify indicators, or markers indicative of $PEEP_i$. In an aspect of the invention, a neural network 24 may be provided to model the parameters so that a ventilator may be controlled through controller 26.

The approach to measuring $PEEP_i$ relies on monitoring several different patient parameters in real-time. The concept entails measuring the "markers" that indicate the presence of $PEEP_i$, and feeding those qualified markers into a neural network, linear regression model, or the like. A value for $PEEP_i$ is then predicted by using all of the different markers detected using methods best described as akin to a neural network, linear multiple regression modeling, or nonlinear multiple regression modeling. If a neural network model is used, the network is "pre-trained" using actual clinical data collected from patients suffering with varying degrees of $PEEP_i$ —levels that have been measured as accurately as possible using an esophageal balloon. $PEEP_i$ measured via the esophageal balloon technique ($PEEP_{i,pes}$) is considered a reference or, true $PEEP_i$. The $PEEP_{i,pes}$ is used for training of the neural network as well as for validation of the approach. The neural network is trained to predict the actual $PEEP_i$ using the PEEPi markers as input parameters.

Examples of $PEEP_i$ markers include:

Sudden flow reversal marking end-exhalation.

Frequent volume channel "resets" at end-exhalation. This occurs because modern volume measuring equipment starts from zero volume at each breath.

Spikes at onset of expiratory flow accompanied by at least two distinct expiratory flow decay patterns.

Continuous increase in end-tidal carbon dioxide ($ETCO_2$) regardless of the expiratory time.

High total respiratory system resistance and compliance, along with high breathing rates or elevated tidal volumes; since the product of total resistance and compliance equals the time constant for the lungs (60% of the volume above the $V_r$ will be exhaled in the interval of one time constant), the greater the time constant, the greater the chance the patient will exhibit $PEEP_i$, particularly when breathing rapidly or when taking large breaths Additional markers have been discovered, forming the backbone of the invention, that provide information related to the magnitude and type of $PEEP_i$. These markers estimate $PEEP_i$ based on flow/volume trajectory, carbon dioxide ($CO_2$) flow/volume trajectory, $CO_2$/volume ratio, expiratory flow at onset of inhalation, and modeling on expiratory waveform. Many of these markers are unique and by themselves can be used to measure PEEPi. However, a combination of two or more of the markers may provide a more robust and accurate measure.

Figure 2A:
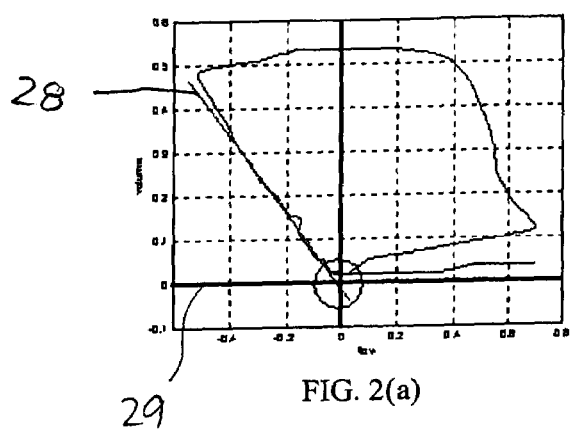
FIG. 2a depicts a graph of a flow/volume loop in subjects without $PEEP_i$.
Figure 2:
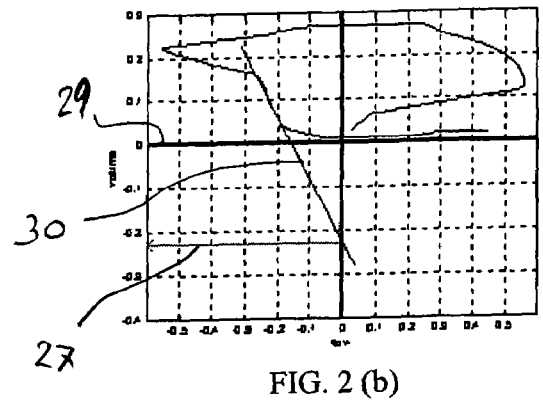
FIG. 2b depicts a graph of a flow/volume loop in subjects with $PEEP_i$.

Now, referring to FIGS. 2a and 2b, it follows that the flow/volume trajectory relies on analyzing the expiratory flow and volume of each breath. Under normal conditions, a plot of expiratory flow versus volume results in a nearly straight line 28 that intersects the volume axis 29 at approximately zero (FIG. 2a). That is, at end-exhalation the volume of gas coming out of the lungs is zero. The slope of the flow/volume trajectory is related to the average time constant of the lungs. A typical flow/volume loop for patients with $PEEP_i$ is shown in FIG. 2b. In this particular case, the trajectory line 30 intersects the volume axis 29 at well below zero; this indicates that had the exhalation phase continued, an additional 0.24 L (y-axis intercept 27) of gas would have been expelled from the lungs. Dividing the additional gas volume by the patient's respiratory compliance yields a quantifiable inference of the $PEEP_i$ pressure.

Figure 3:
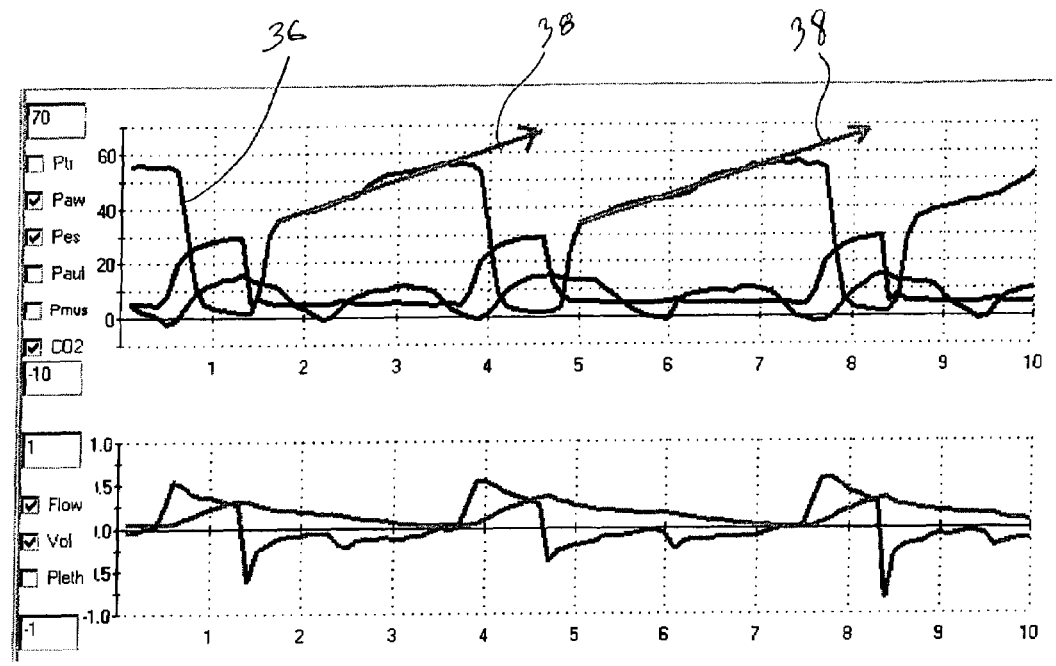
FIG. 3 depicts a temporal plot of rising $CO_2$ during exhalation.
Figure 4A:
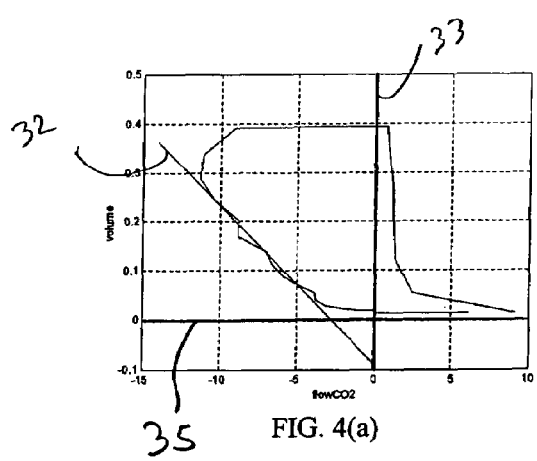
FIG. 4a depicts a graph of flow $CO_2$/volume loop in subjects without $PEEP_i$.
Figure 4B:
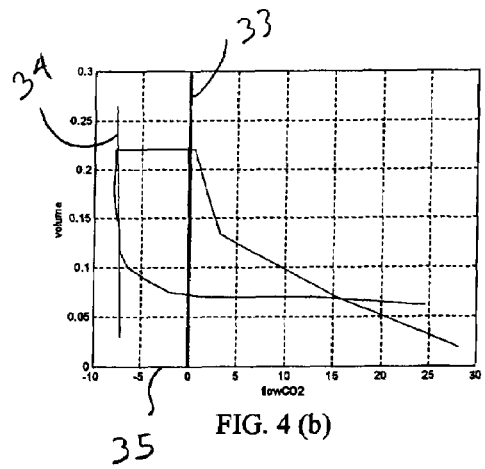
FIG. 4b depicts a graph of flow $CO_2$/volume loop in subjects with $PEEP_i$.

$CO_2$ flow/volume trajectory is similar to the flow/volume trajectory, except $CO_2$ flow 36 is plotted as shown in FIG. 3 instead of exhaled flow. $CO_2$ flow is obtained by multiplying the exhaled $CO_2$ and exhaled flow. In some $PEEP_i$ patients, the exhaled $CO_2$ tends to continue to rise when there is very minimal exhalation flow (FIG. 3). The $CO_2$ flow parameter captures this rising $CO_2$ trend 38, and when plotted against volume as shown in FIG. 4b, results in a trajectory 34 that often parallels the volume axis 33 for $PEEP_i$ patients. FIGS. 4a and 4b illustrate a comparison between patients that have and do not have $PEEP_i$, respectively. In non-$PEEP_i$ patients as shown in FIG. 4a, the trajectory 32 eventually intersects near the point where the volume 33 and flow 35 axes meet. The slope of the trajectories 32, 34 can provide an indication to the severity of $PEEP_i$, where steep slopes such as shown in FIG. 4b indicate severe $PEEP_i$ and shallow slopes such as shown in FIG. 4a indicate low levels of $PEEP_i$.

$CO_2$/volume ratio, another $PEEP_i$ marker, is a fractional value of exhaled CO2 divided by exhaled volume. The maximum exhaled CO2 value and the change in volume during exhalation are computed for each breath. The ratio is given by:

$$CO_2/volume_{ratio} = \max(ETCO_2)/volume_{exhaled}$$

It has been observed that $PEEP_i$ patients have a larger ratio value versus those patients who do not have $PEEP_i$.

The fourth of the additional $PEEP_i$ markers, expiratory flow at the onset of inhalation, attempts to capture the exhaled flow rate at precise moment of end-exhalation by locating the onset of an inhalation effort. If gas is still flowing out of the lungs at the onset of inhalation, it can be reasoned that the only force driving this gas flow, at this instant in time, is $PEEP_i$.

$PEEP_i$ at the onset of inhalation ($PEEP_{i,onset}$), is estimated using the product of the expiratory airflow at inhalation onset ($flow_{onset}$) and resistance to airflow produced by the airways of the lungs ($R_{aw}$).

$$PEEP_{i,onset} = flow_{onset} \times R_{aw}$$

Total respiratory resistance ($R_{total}$) is traditionally determined by programming the patient's ventilator to produce an end-inspiratory pause (usually the pause lasts 0.5 sec. or more) when delivering any mandated breath—these are breaths where the operator, not the patient, determines the gas flow rate, the gas flow pattern, the tidal volume and the frequency at which they are delivered/min. During each mandated breath, the difference between the peak inflation pressure (PIP) and the plateau pressure ($P_{plat}$) is determined. The difference is divided by the airflow measured at the moment the PIP was observed. It is also traditional to perform this measurement using a square flow pattern and with the gas flow programmed at or very near to 60 liters/min (1 liter/sec). This is done because resistance is defined as the pressure drop (measured in cm $H_2O$) when gas is flowing at precisely 60 liters/min (1 liter/sec). Symbolically, resistance is determined as follows:

$$R_{aw} = (PIP - P_{plat})/flow.$$

As defined above, resistance, computed in this manner, represents the total resistance of the respiratory system, and is acceptable as long as both lungs have similar resistance values.

During an end-inspiratory pause, since gas cannot escape from the lungs, it gradually redistributes from the hyperinflated alveoli to under-inflated alveoli—a process called pendelluft.

Figure 5:
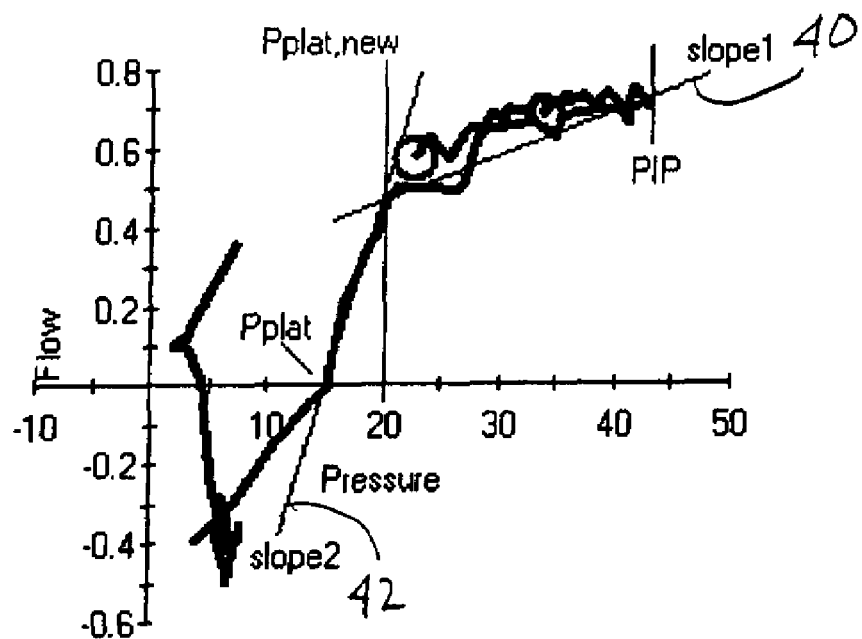
FIG. 5 depicts a graph of isolation of pressure drop due to airway.

Resistance to airflow (only) can be isolated from most PIP to $P_{plat}$ pressure differences, by analyzing the flow versus pressure loop for that specific breath. In the presence of pendelluft, the expiratory side of the loop contains two distinct flow-pressure decay rates or slopes (FIG. 5). The first slope 40, in which pressure changes very rapidly (slope 1 40 in FIG. 5), is due to the resistance the airways produce; the second slope 42 (slope 2 in FIG. 5), the much slower rate of pressure change, is from the redistribution of gases. The difference in pressure drop between PIP and the pressure obtained from first decay rate ($P_{plat,new}$) represents the differential airway pressure used to determine airflow resistance only. Raw is then obtained by dividing difference between the PIP and $P_{plat,new}$ by the measured flow at the moment PIP was reached.

Another marker is a mathematical modeling of an expiratory waveform that estimates the respiratory system time constant (the product of resistance and compliance) changes during the course of exhalation. The concept is to get a better measure of system dynamics and, to predict $PEEP_i$. Two modeling techniques have been explored: 1) estimate of system time constant and lung compliance using least squares, and 2) modeling resistance using an exponential function. Both methods rely on similar principles.

Figure 6:
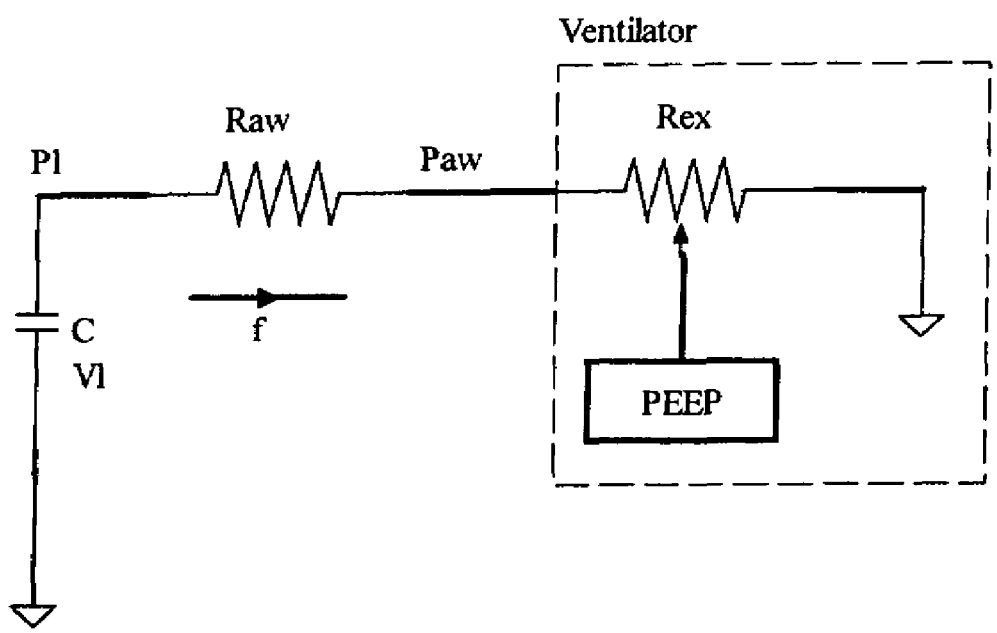
FIG. 6 depicts a simplified electrical circuit representing a patient's respiratory system when receiving support provided by a ventilator.

The respiratory system and a patient's ventilator can be represented using an electrical circuit diagram (FIG. 6). Table 1 below lists the definition of terms used in FIG. 6:

TABLE 1

| | |
|---|---|
| C | lung compliance |
| $V_l$ | lung volume |
| f | flow |
| $R_{aw}$ | airway resistance |
| $R_{ex}$ | ventilator exhalation valve resistance |
| $P_l$ | lung pressure |
| $P_{aw}$ | airway pressure |

Airway pressure and flow are measured at the patient mouth by a differential pressure transducer. The corresponding gas volume ($V_{nico}$) from the measured flow is computed by integration of flow over the exhalation time period. The ventilator exhalation resistance changes based on ventilator PEEP setting to maintain $P_{aw}$ at PEEP pressure at the end of exhalation.

With reference to FIG. 6, an estimate of system time constant and lung compliance using least squares as follows:

During exhalation, flow is defined as:

$$f(t)=(P_l(t)-P_{aw}(t))/R_{aw},$$

the lung pressure can be represented as lung volume divided by lung compliance, so flow can be written as:

$$f(t) = \left(\frac{V_l(t)}{C} - P_{aw}(t)\right) / R_{aw},$$

and rearranged to represent lung volume as:

$$V_l(t)=\tau*f(t)+C*P_{aw}(t),$$

where $\tau$ is the time constant and defined as:

$$\tau=R_{aw}C.$$

The lung volume above the functional residual capacity (FRC) of the lung can be approximated as the summation of the actual measured gas volume inhaled by patient, volume due to PEEP, and any trapped gas.

$$V_l(t)=V_{nico}(t)+V_{PEEP}+V_{PEEPi}$$

So, lung volume can now be described as:

$$V_{nico}(t)=\tau*f(t)+C*P_{aw}(t)-V_{PEEP}-V_{PEEPi}$$

Since volume due to PEEP and $PEEP_i$ are constant, they can be eliminated from the equation by observing only differential changes.

$$\Delta V_{nico}=\tau*\Delta f+C*\Delta P_{aw}$$

The time constant and compliance are solved by least squares analysis. Volume due to PEEP and $PEEP_i$ can be computed as:

$$V_{PEEP}+V_{PEEPi}=\tau*f(t)+C*P_{aw}(t)-V_{nico}(t)$$

$PEEP_i$ pressure can then be easily computed from:

$$PEEP_i = \frac{V_{PEEP} + V_{PEEPi}}{C} - PEEP$$

Modeling resistance using an exponential function is performed as follows:

During exhalation, lung pressure can be described as:

$$P_l(t)=P_{aw}(t)+R_{aw}*f(t)$$

Flow can be described by an exponential decaying waveform during exhalation as:

$$f(t)=f_0*e^{-t/R_{aw}C}$$

and solved for $R_{aw}$ by:

$$R_{aw} = -\frac{t}{C*\ln(f(t)/f_0)}$$

The lung pressure can then be described as:

$$P_l(t) = P_{aw}(t) - f(t) * \frac{t}{C*\ln(f(t)/f_0)}$$

From this equation, the $PEEP_i$ pressure can be estimated by calculating the difference in lung pressure between the inhalation onset ($t_{onset}$) and location at zero flow ($t_{end}$).

$$PEEP_i=P_l(t_{onset})-P_l(t_{end})$$

Inhalation onset can be detected as described previously (flow onset marker) or by observing the $P_l$ itself, which goes through a sudden slope change at onset.

This $PEEP_i$ estimate was done based on the assumption that 1) lung compliance remains fixed during exhalation, and 2) flow during exhalation decays exponentially. A slight variation of this method assumes that resistance remains fixed during exhalation, instead of lung compliance. In this case, the lung pressure is defined by modeling the lung compliance.

Peak to Mid-Exhalation Flow Ratio. This marker is calculated by dividing the peak exhalation flow by the flow calculated when about 20% to 30%, and preferably, about 25%, of the tidal volume remains in the lungs (75% has been exhaled). Flow limitation patients have high peak flows that decay very rapidly. This parameter will be large when the exhaled flow decays very quickly, indicating flow limitation.

Description of Neural Networks

Artificial neural networks loosely model the functioning of a biological neural network, such as the human brain. Accordingly, neural networks are typically implemented as computer simulations of a system of interconnected neurons. In particular, neural networks are hierarchical collections of interconnected processing elements (PEs). These elements are typically arranged in layers, where the input layer receives the input data, the hidden layers transform the data, and the output layer produces the desired output. Other embodiments of a neural network can also be used.

Each processing element in the neural network receives multiple input signals, or data values, that are processed to compute a single output. The inputs are received from the outputs of PEs in the previous layer or from the input data. The output value of a PE is calculated using a mathematical equation, known in the art as an activation function or a transfer function that specifies the relationship between input data values. As known in the art, the activation function may include a threshold, or a bias element. The outputs of elements at lower network levels are provided as inputs to elements at higher levels. The highest level element, or elements, produces a final system output, or outputs.

Figure 7:
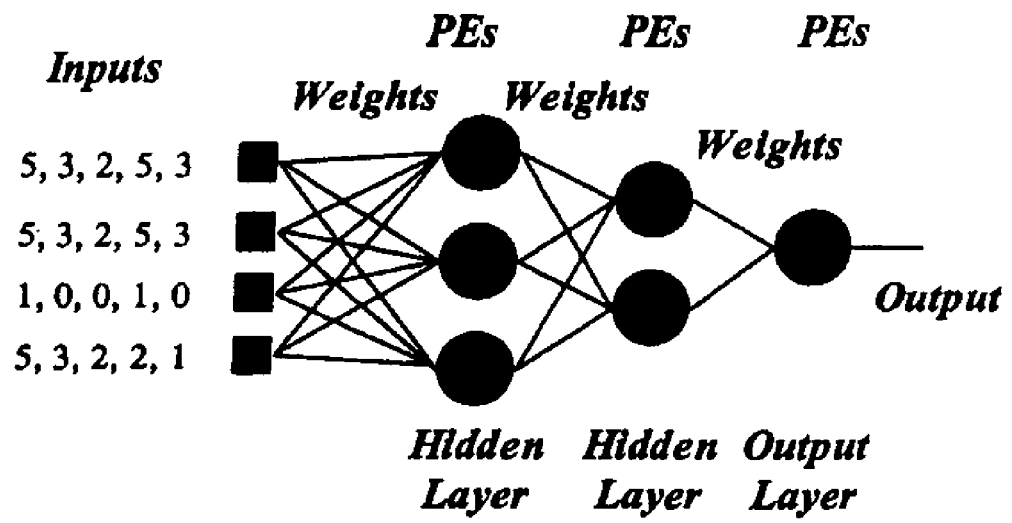
FIG. 7 depicts an exemplary neural network architecture

In the context of the present invention, the neural network is a computer simulation that is used to produce a noninvasive estimate of the quantified intrinsic PEEP described previously. The neural network of the present invention may be constructed by specifying the number, arrangement, and connection of the processing elements which make up the network. A simple embodiment of a neural network consists of a fully connected network of processing elements. As shown in FIG. 7, the processing elements of the neural network are grouped into layers: an input layer where the parameters collected and/or derived from the airway pressure and flow sensors are inputted to the network; a hidden layer of processing elements; and an output layer where the resulting prediction of intrinsic PEEP is produced. The number of connections, and consequently the number of connection weights, is fixed by the number of elements in each layer.

Figure 8:
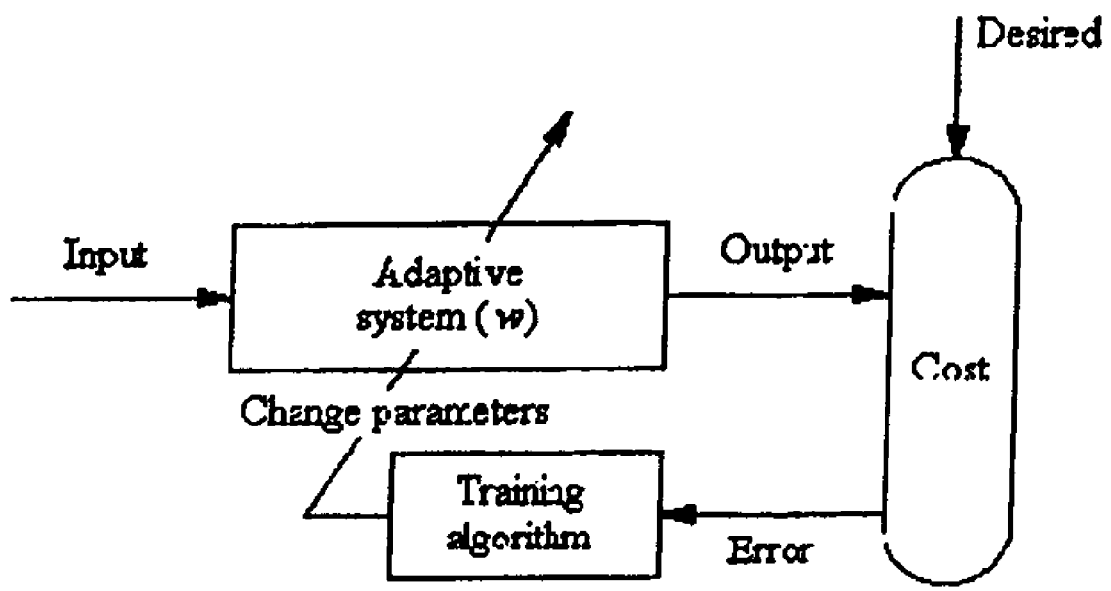
FIG. 8 depicts inputs and outputs of an adaptive system having backpropagation.

The most common training methodology for neural networks is based upon iterative improvement of the system parameters (normally called weights) by minimizing the mean squared difference between the desired output and the network output (mean squared error, MSE). The input is applied to the neural network, the neural network passes the data through its hierarchical structure, and an output is created. This network output is compared with the desired output corresponding to that input and an error is calculated. This error is then used to adjust the weights of the system so that the next time that particular input is applied to the system the network output will be closer to the desired output. There are many possible methodologies to adjust the weights, called the training algorithm. As shown in FIG. 8, the most common is called backpropagation that involves calculating each weight's responsibility for the error, and calculating a local gradient from this error in order to use a gradient descent learning rule for each weight.

Based on the foregoing specification, the invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

One skilled in the art of computer science will easily be able to combine the software created as described with appropriate general purpose or special purpose computer hardware to create a computer system or computer sub-system embodying the method of the invention. An apparatus for making, using or selling the invention may be one or more processing systems including, but not limited to, a central processing unit (CPU), memory, storage devices, communication links and devices, servers, I/O devices, or any subcomponents of one or more processing systems, including software, firmware, hardware or any combination or subset thereof, which embody the invention. User input may be received from the keyboard, mouse, pen, voice, touch screen, or any other means by which a human can input data into a computer, including through other programs such as application programs.

What is claimed is:

1. A method for detecting and quantifying intrinsic positive end-expiratory pressure of a respiratory patient breathing with the assistance of a ventilator comprising:
   receiving respiratory airway data from one or more sensors adapted to non-invasively monitor a respiratory patient;
   calculating from the respiratory airway data two or more parameters that are indicative of or quantify intrinsic positive end-expiratory pressure of the patient;
   inputting the two or more parameters that are indicative of or quantify intrinsic positive end-expiratory pressure into a mathematical model;
   generating by the mathematical model a predicted quantitative value for intrinsic positive end-expiratory pressure representing an excess lung volume of the patient based on the two or more parameters; and
   providing a variable to a ventilator or respiratory monitor based on the predicted quantitative value for intrinsic positive end-expiratory pressure.

2. The method of claim 1, wherein the two or more parameters that are indicative of or quantify intrinsic positive end-expiratory pressure are calculated in accordance with predetermined markers of intrinsic positive end-expiratory pressure.

3. The method of claim 2, further comprising using the predicted quantitative value for intrinsic positive end-expiratory pressure in diagnosis of the patient who may be experiencing intrinsic positive end-expiratory pressure.

4. The method of claim 3, further comprising using the predicted quantitative value for intrinsic positive end-expiratory pressure to adjust a ventilator setting.

5. The method of claim 3, further comprising using the predicted quantitative value for intrinsic positive end-expiratory pressure to generate display indicia.

6. The method of claim 3, further comprising using one of the parameters to calculate a different parameter.

7. The method of claim 2, further comprising using the predicted quantitative value for intrinsic positive end-expiratory pressure in treatment of the patient experiencing intrinsic positive end-expiratory pressure.

8. The method of claim 2, wherein the predetermined markers comprise one or more of an expiratory air flow versus expiratory air volume trajectory, an expiratory carbon dioxide flow versus expiratory air volume trajectory, an expiratory carbon dioxide volume to expiratory air volume ratio, an expiratory air flow at onset of inhalation, a model of an expiratory waveform, a peak to mid-exhalation airflow ratio, duration of reduced exhaled airflow, and a Capnograph waveform shape.

9. The method of claim 8, further comprising using a characteristic of the expiratory air flow versus expiratory air volume trajectory as a parameter indicative of a positive end-expiratory pressure condition.

10. The method of claim 8, further comprising using a characteristic of the expiratory carbon dioxide flow versus air volume trajectory as a parameter indicative of a positive end-expiratory pressure condition.

11. The method of claim 8, wherein the expiratory carbon dioxide to expiratory air volume ratio is derived from an elevated end tidal carbon dioxide flow and expiratory air volume of a breath of a patient.

12. The method of claim 8, wherein the expiratory air flow at onset of inhalation is derived from an airflow at onset of inhalation of the patient and a resistance to airflow produced by the airways of the lungs of a patient being tested.

13. The method of claim 8, wherein the model of the expiratory waveform is derived using a least squares analysis.

14. The method of claim 8 wherein the model of the expiratory waveform is derived using an exponential function analysis.

15. The method of claim 8, wherein the peak to mid-exhalation airflow ratio is derived using a peak exhalation air flow and an expiratory air flow calculated when about 20% to 30% of a tidal air volume remains in the lungs of a patient.

16. The method of claim 8, further comprising using a characteristic of the Capnograph waveform shape as a parameter indicative of a positive end-expiratory pressure condition.

17. The method of claim 16, wherein the characteristic comprises a rising slope occurring after an increased rise time in an expiratory carbon dioxide flow.

18. The method of claim 2,
wherein the mathematical model is created using clinical data.

19. The method of claim 18, wherein the mathematical model is selected from the group consisting of a neural network model, a fuzzy logic model, a mixture of experts model, or a polynomial model.

20. The method of claim 18, wherein the mathematical model is a neural network trained to provide said at least one output variable, wherein the training of the neural network comprises clinical testing of a test population of patients using two or more parameters calculated from respiratory airway data of respective patients as clinical data input to the neural network.

21. The method of claim 1, wherein the respiratory airway data comprise one or more of airway pressure, airway flow, airway volume, and end-tidal carbon dioxide flow.

22. A system for detecting and quantifying intrinsic positive end-expiratory pressure of a respiratory patient comprising:
a signal processor for non-invasively collecting data corresponding to a patient's expiratory effort while spontaneously breathing with assistance of a ventilator; and
a parameter extraction module for calculating two or more parameters that are indicative of or quantify intrinsic positive end-expiratory pressure from the data used in estimating intrinsic positive end-expiratory pressure;
an adaptive processor for modeling the patient's intrinsic positive end-expiratory pressure PEEPi from the two or more parameters to derive a predicted quantitative value for PEEPi representing an excess lung volume of the patient and providing a variable based on the predicted quantitative value for intrinsic positive end-expiratory pressure; and
a controller for providing the variable to a ventilator or respiratory monitor.

23. A method for detecting and quantifying intrinsic positive end-expiratory pressure of a respiratory patient breathing with the assistance of a ventilator, comprising:
receiving respiratory airway data from one or more sensors adapted to non-invasively monitor a patient, wherein the respiratory data comprise one or more of airway pressure, airway flow, airway volume, and carbon dioxide flow;
calculating from the respiratory airway data two or more parameters that are indicative of or quantify intrinsic positive end-expiratory pressure of the patient based on predetermined markers, wherein said markers comprise one or more of an expiratory air flow versus expiratory air volume trajectory, an expiratory carbon dioxide flow versus expiratory air volume trajectory, an expiratory carbon dioxide volume to expiratory air volume ratio, an expiratory air flow at onset of inhalation, a model of an expiratory waveform, a peak to mid-exhalation airflow ratio, duration of reduced exhaled airflow, and a Capnograph waveform shape;
inputting the two or more parameters that are indicative of or quantify intrinsic positive end-expiratory pressure into a mathematical model;
generating by the mathematical model a predicted quantitative value for intrinsic positive end-expiratory pressure representing an excess lung volume of the patient based on the two or more parameters; and
providing a variable to a ventilator or respiratory monitor based on the predicted quantitative value for intrinsic positive end-expiratory pressure.

24. The method of claim 23, further comprising using the predicted quantitative value for intrinsic positive end-expiratory pressure for diagnosing the patient who may be experiencing intrinsic positive end-expiratory pressure.

25. The method of claim 23,
wherein the mathematical model is configured from clinical data for predicting intrinsic positive end-expiratory pressure.

26. An apparatus for detecting and quantifying intrinsic positive end-expiatory pressure of a respiratory patient breathing with the assistance of a ventilator comprising:
a sensor for non-invasively monitoring respiratory airway data of a patient; and
a processing device for calculating from the respiratory airway data two or more parameters that are indicative of or quantify intrinsic positive end-expiratory pressure of the patient based on predetermined markers;
inputting the two or more parameters that are indicative of or quantify intrinsic positive end-expiratory pressure into a mathematical modeling device;
deriving by the mathematical modeling device a predicted quantitative value for an intrinsic positive end-expiratory pressure representing an excess lung volume of the patient based on the two or more parameters; and
providing a variable to a ventilator or respiratory monitor based on the predicted quantitative value for intrinsic positive end-expiratory pressure.

27. The apparatus of claim 26, wherein the respiratory airway data comprise one or more of airway pressure, airway flow, airway volume, and carbon dioxide flow, and wherein the predetermined markers comprises one or more of an expiratory air flow versus expiratory air volume trajectory, an expiratory carbon dioxide flow versus expiratory air volume trajectory, an expiratory carbon dioxide volume to expiratory air volume ratio, an expiratory air flow at onset of inhalation, a model of an expiratory waveform, a peak to mid-exhalation airflow ratio, duration of reduced exhaled airflow, and a Capnograph waveform shape.

28. The apparatus of claim 26
wherein the mathematical modeling device is created using clinical data.

29. The apparatus of claim 28, wherein the mathematical modeling device is a neural network trained to provide said at least one output variable, wherein the training of the neural network comprises clinical testing of a test population of patients using two or more parameters that are indicative of or quantify intrinsic positive end-expiratory pressure calculated from the respiratory airway data of respective patients as clinical data input to the neural network.

30. A system for detecting and quantifying intrinsic positive end-expiratory pressure of a respiratory patient breathing with the assistance of a ventilator, comprising:

means for non-invasively measuring respiratory data of the patient, wherein the respiratory data comprise one or more of airway pressure, airway flow, airway volume, and carbon dioxide flow;

means for calculating two or more parameters that are indicative of or quantify intrinsic positive end-expiratory pressure from the respiratory data;

means for inputting the two or more parameters that are indicative of or quantify intrinsic positive end-expiratory pressure into a mathematical model;

means for deriving by the mathematical model a predicted quantitative value for an intrinsic positive end-expiratory pressure representing an excess lung volume of the patient based on the two or more parameters; and means for providing a variable to a ventilator or respiratory monitor based on the predicted quantitative value for intrinsic positive end-expiratory pressure.

31. The system of claim 30, wherein the two or more parameters that are indicative of or quantify intrinsic positive end-expiratory pressure of the patient are based on predetermined markers comprising two or more of an expiratory air flow versus expiratory air volume trajectory, an expiratory carbon dioxide flow versus expiratory air volume trajectory, an expiratory carbon dioxide volume to expiratory air volume ratio, an expiratory air flow at onset of inhalation, a model of an expiratory waveform, a peak to mid-exhalation airflow ratio, duration of reduced exhaled airflow, and a Capnograph waveform shape.

32. The system of claim 30, further comprising:
means for predicting effort of breathing using the mathematical model created using clinical data.

33. The system of claim 32, wherein the mathematical model is a neural network trained to provide said at least one output variable, wherein the training of the neural network comprises clinical testing of a test population of patients using two or more parameters that are indicative of or quantify intrinsic positive end-expiratory pressure calculated from respiratory data at the mouth of respective patients as clinical data input to the neural network.

34. A tangible computer readable medium for detecting and quantifying intrinsic positive end-expiratory pressure of a respiratory patient breathing with assistance of a ventilator, comprising:

code devices for receiving non-invasively measured respiratory data of the patient;

code devices for calculating two or more parameters that are indicative of or quantify intrinsic positive end-expiratory pressure from the respiratory data;

code devices for simultaneously inputting the two or more parameters that are indicative of or quantify intrinsic positive end-expiratory pressure into a mathematical model comprising a linear model or a non-linear model;

code devices for deriving by the mathematical model a predicted quantitative value for an intrinsic positive end-expiratory pressure representing an excess lung volume of the patient based on the two or more parameters; and code devices for providing a variable to a ventilator or respiratory monitor based on the predicted quantitative value for intrinsic positive end-expiratory pressure.

35. The tangible computer readable medium of claim 34, wherein the two or more parameters that are indicative of or quantify intrinsic positive end-expiratory pressure are based on predetermined markers comprising at least two of expiratory air flow versus expiratory air volume trajectory, an expiratory carbon dioxide flow versus expiratory air volume trajectory, an expiratory carbon dioxide volume to expiratory air volume ratio, an expiratory air flow at onset of inhalation, a model of an expiratory waveform, a peak to mid-exhalation airflow ratio, duration of reduced exhaled airflow, and a Capnograph waveform shape.

36. The tangible computer readable medium of claim 34, further comprising:
code devices for predicting effort of breathing using the mathematical model created using clinical data.

37. The tangible computer readable medium of claim 36, wherein the mathematical model is a neural network trained to provide said at least one output variable, wherein the training of the neural network comprises clinical testing of a test population of patients using two or more parameters calculated from respiratory data of airway flows at the mouth of respective patients as clinical data input to the neural network.

* * * * *